US008939915B2

(12) United States Patent
Sjunnesson et al.

(10) Patent No.: US 8,939,915 B2
(45) Date of Patent: Jan. 27, 2015

(54) SURGICAL KITS AND METHODS (75) Inventors: Håkan Sjunnesson, Stockholm (SE); Per Hedèn, Stockholm (SE)

(73) Assignee: Novoaim AB, Stockholm (SE)

( * ) Notice: Subject to any disclaimer, the term of this patent is extended or adjusted under 35 U.S.C. 154(b) by 221 days.

(21) Appl. No.: 12/670,598

(22) PCT Filed: Jun. 5, 2008

(86) PCT No.: PCT/SE2008/050672
§ 371 (c)(1), (2), (4) Date: Jan. 25, 2010

(87) PCT Pub. No.: WO2009/017445
PCT Pub. Date: Feb. 5, 2009

(65) Prior Publication Data
US 2010/0210967 A1 Aug. 19, 2010

Related U.S. Application Data (60) Provisional application No. 60/964,911, filed on Aug. 15, 2007.

(30) Foreign Application Priority Data

Aug. 2, 2007 (SE) ...................................... 0701811

(51) Int. Cl.
*A61B 5/00* (2006.01)
(52) U.S. Cl.
USPC ........................................................ 600/564
(58) Field of Classification Search
USPC ............ 600/564–567; 606/187, 224; 623/902
See application file for complete search history.

(56) References Cited

U.S. PATENT DOCUMENTS

| 2,541,542 | A | | 12/1946 | Perez at al. | |
|---|---|---|---|---|---|
| 5,133,360 | A | | 7/1992 | Spears | |
| 5,211,644 | A | | 5/1993 | VanBeek et al. | |
| 5,269,316 | A | | 12/1993 | Spitalny | |
| 5,382,257 | A | * | 1/1995 | Lewis et al. | 606/148 |
| 5,687,739 | A | | 11/1997 | McPherson et al. | |
| 5,817,034 | A | | 10/1998 | Milliman et al. | |
| 5,857,982 | A | | 1/1999 | Milliman et al. | |
| 5,888,202 | A | * | 3/1999 | Amiri | 623/15.11 |
| 6,077,230 | A | | 6/2000 | Gregoire et al. | |
| 6,162,203 | A | | 12/2000 | Haaga | |
| 6,440,141 | B1 | | 8/2002 | Philippon | |
| 6,767,354 | B2 | * | 7/2004 | Johanson et al. | 606/179 |

(Continued)

FOREIGN PATENT DOCUMENTS

| CN | 2902203 Y | 5/2007 |
|---|---|---|
| EP | 0 609 239 B1 | 3/2000 |

(Continued)

OTHER PUBLICATIONS

Fagrell, et al., "Fat Cylinder Transplantation: An Experimental Comparative Study of Three Different Kinds of Fat Transplants," *Plastic and Reconstructive Surgery*, vol. 98, pp. 90-96, Jul. 1996.

*Primary Examiner* — Max Hindenburg
(74) *Attorney, Agent, or Firm* — Dickstein Shapiro LLP (57) ABSTRACT

A kit for implantation of material into a body, a kit for extraction of tissue from a body and a tissue transplantation kit. A method for implanting material into a body, a method for extracting tissue from a body and a method for transplanting tissue into a body.

9 Claims, 7 Drawing Sheets

(56) References Cited

U.S. PATENT DOCUMENTS

| | | | |
|---|---|---|---|
| 7,052,495 B2 * | 5/2006 | Smith | 606/47 |
| 7,115,125 B2 * | 10/2006 | Nakao et al. | 606/47 |
| 7,166,133 B2 * | 1/2007 | Evans et al. | 623/23.51 |
| 7,422,596 B2 * | 9/2008 | Therin et al. | 606/232 |
| 7,452,367 B2 * | 11/2008 | Rassman et al. | 606/187 |
| 7,601,125 B1 | 10/2009 | Kai | |
| 7,608,048 B2 * | 10/2009 | Goldenberg | 600/564 |
| 7,621,934 B2 * | 11/2009 | Bodduluri et al. | 606/187 |
| 7,828,745 B2 * | 11/2010 | McAlister et al. | 600/566 |
| 8,038,595 B2 * | 10/2011 | Laham et al. | 600/37 |
| 8,105,243 B2 * | 1/2012 | Vetter | 600/564 |
| 2002/0111603 A1 | 8/2002 | Cheikh | |
| 2002/0188196 A1 | 12/2002 | Burbank et al. | |
| 2003/0036770 A1 * | 2/2003 | Markman | 606/187 |
| 2003/0097079 A1 | 5/2003 | Garcia | |
| 2003/0236573 A1 | 12/2003 | Evans et al. | |
| 2004/0199120 A1 | 10/2004 | Lohr et al. | |
| 2004/0210245 A1 | 10/2004 | Erickson et al. | |
| 2005/0090852 A1 | 4/2005 | Layne et al. | |
| 2007/0106307 A1 | 5/2007 | Bodduluri et al. | |
| 2008/0234697 A1 | 9/2008 | DuBois | |
| 2010/0082042 A1 | 4/2010 | Drews | |

FOREIGN PATENT DOCUMENTS

| | | |
|---|---|---|
| EP | 0 794 733 B1 | 4/2003 |
| UA | 2 199 247 A | 7/1988 |
| WO | WO 00/02616 A1 | 1/2000 |

* cited by examiner

SURGICAL KITS AND METHODS

This is a 371 of International Application No. PCT/SE2008/050672, filed on Jun. 5, 2008, which claims the benefit of Swedish Application No. 0701811-2, filed on Aug. 2, 2007 and U.S. Provisional Application Ser. No. 60/964,911, filed on Aug. 15, 2007.

FIELD OF TECHNOLOGY

The present invention concerns an extraction kit, an implantation kit and a transplantation kit. The invention also concerns a method for extracting tissue, a method for implanting material and a method for transplanting tissue.

Any material suitable to be implanted in a body may be implanted in a body by means of the implantation kit and the method for implanting material. Preferably, tissue is implanted, such as muscles, corium, dermis, bone, cartilage and fat.

Any tissue may be extracted from the body by means of the extraction kit and the method for extracting tissue. Transplantation of tissue may be carried out by means of using the transplantation kit and the method for transplantation of tissue.

BACKGROUND AND PRIOR ART

Transplantation of fat carried out today is mostly done by fat suction from a body, centrifuging/cleaning the fat in order to achieve a concentrate of fat cells and injecting the concentrate into the body, preferably by means of an injection needle. The problem concerning this method of transplanting is that 60-100% of the injected fat will be absorbed by the body within a year.

It is known that segmental or core fat, i.e. fat not being centrifuged/cleaned but with intact morphology/structure, will not be absorbed in a corresponding way when it is transplanted into a body. Studies on animals have shown a degree of absorption below 5%. See Fagrell, D.; Enestrom, S.; Berggren, A., et al. Fat cylinder transplantation: An experimental comparative study of three different kinds of fat transplants. Plastic and Reconstructive Surgery 98: 90, 1996.

One problem with transplanting tissue is the difficulty in extracting tissue of suitably small dimensions. Another problem concerns implanting the tissue with sufficient precision.

U.S. Pat. No. 5,269,316 shows a surgical instrument for removal, transplantation or implantation of corium, fat, cartilage or alloplastic material. The instrument is composed of three severable adjacent sections, the first which is a hollow scalpel, the second a hollow tube in communication with the hollow scalpel and the third is a solid portion tapered to a sharp needle.

The hollow scalpel and the solid sharp needle are severable from an end each of the hollow tube and the hollow tube is separable along its length after removal of the hollow scalpel and the sharp needle portion.

When using the instrument the sharp needle portion is fastened in a surgical drill so that the hollow scalpel can be introduced into a body through the skin at a first position, in a drilling fashion, and through the tissue to be extracted and finally out through the skin at a second position, thus making two wounds in the skin. It is difficult to see how this could work in practise since there seems not to be any evacuation of air from the inside of the hollow tube so when the tissue to be extracted should move into the hollow tube it will soon be stopped by an air cushion present inside the hollow tube.

Thereafter, the instrument is removed from the drill, turned and fastened at the hollow scalpel instead. Now the drilling starts with the sharp needle portion at the position of the body were the implantation is to be carried out. The instrument is introduced through the skin at a first position, along the path for transplantation and out through the skin again at a second position, thus making another set of two wounds in the skin.

The drill is removed and the hollow scalpel and the sharp needle portion are severed from the hollow tube, which is positioned inside the body. The hollow tube is then split into two halves still inside the body and withdrawn from the body leaving the transplanted tissue inside the body. It seems to be rather difficult to perform this separation and it will also cause an enlargement of the implantation cavity during the separation of the two parts as they need to be pushed radially away from each other in order to severe the two parts.

A problem with this surgical instrument is that it makes two holes in the skin, both when extracting tissue and when implanting tissue. Another problem is that the needle portion is sharp causing the tissue around the implanted tissue to bleed, which endanger the result of the transplantation increasing the risk of necrosis and/or rejection of the implanted tissue by the body. It also increases the risk of nerve, blood vessels and surrounding tissue injuries. Overall it seems to be a very circumstantial method.

In a recent article a new method is described for extracting core fat and implanting it. The article was published in Plastic and Reconstructive Surgery July 2007. It is called Facial Augmentation with Core Fat Graft: A Preliminary Report by Bahman Guyuron and Ramsey K. Majzoub.

The authors of the article have taken a 1 ml syringe and obliquely cut off the tip with an oscillating saw. A small incision was made in the extraction site of the body and the surgeon rotated and advanced the syringe while gently pulling the syringe piston to accommodate the fat.

A pair of baby Metzenbaum scissors or the same syringe containing the extracted fat was used to create a space at the implantation site and the syringe was introduced into the space. While the syringe was removed the syringe piston was used to deliver the fat into the newly made space. The syringe was introduced up to four times in the newly made space to deliver about 1 ml core fat per time.

One problem with this method is that it can only be used for fat as the oblique syringe is blunt and that also means it will not work for smaller dimensions either. Another problem is that when creating a space in the tissue at the implantation site the tissue will be severed by the scissors and the scissors will cause a larger inlet opening than needed for the implant and it is difficult to create a longer or deeper space with scissors. Or if the oblique syringe will be pushed into the tissue it will also severe the tissue. The tissue will be traumatized and will bleed. There will also be a risk of injuries to nerves, blood vessels and surrounding tissue.

It will be difficult to fill the space several times, and difficult to find the space each time, especially if it is cut with the scissors. At every time the syringe is inserted into the space there will be a risk of further severing of the tissue. It will be difficult to control the implantation, for example to position the fat at the right position and the right amount.

Placing a strong negative pressure with the syringe piston, which is needed when using a blunt tip, to the extracted fat will traumatize the fat as well as the last step of the extraction when the fat will be torn off the body. It will be impossible to control the extraction of the tissue since it will not be possible to know at which position the fat will be torn off the body, if it will be outside the extraction tube, inside the extraction or at its inner end. Neither will it be possible to control the shape of the extracted tissue as is evident from the picture of the article where the fat has different cross sectional size along its length.

All bleeding at the implantation site or traumatization to the fat will increase the risk of rejection of the fat at the implantation site.

The fat transplantation technique described by Bahman Guyuron and Ramsey K. Majzoub and the clinical results indicate that the method is crude. The extraction technique is limited to certain dimensions of fat tissue that is traumatized and not sharply cut. The fat implantation is likely to produce bleeding at the implantation site and the position of the implanted material is not exactly controlled.

SUMMARY OF THE INVENTION

The kits and methods of this invention aim to solve at least some of these problems.

The present invention concerns a kit for implantation into a body and comprises a penetration rod that may be positioned inside an implantation tube, for making a cavity in the body. The implantation tube maintains the made cavity. The kit also comprises a container, which is insertable into the implantation tube. The container houses the material to be implanted into the made cavity.

By means of this kit it will be possible to implant material by only making one small opening in the skin. It is always an advantage to minimize the opening up of the skin and especially when using the kit in plastic surgery. Another advantage is that the surrounding tissue will be protected by the implantation tube while inserting the container housing the material to be implanted thus decreasing the risk of severing the tissue and facilitate the insertion of the container.

The implantation kit may further comprise a plunger, which would be helpful during removal of the implantation tube and the container to keep the implanted material in place in the made cavity.

The implantation kit can also eliminate the problems of several implantations into the same cavity as a suitable dimension of implantation kit and material and is selected for only one implantation.

A suture and/or having a needle or two may be incorporated into the implantation kit. The suture may also be helpful for keeping the implanted material in place in the made cavity during removal of the implantation tube and container. It could be used instead of the plunger or together with the plunger. It is also possible to draw the material into place in the made cavity by means of the suture. In use the needle will make a needle hole in the skin at a position at a distance from the opening for the implantation. As the person skilled in the art knows, the skin directly closes the needle hole as soon as the needle and suture is removed.

Preferably the penetration rod has a blunt penetration tip. With a blunt penetration tip the penetration rod will separate the tissue while penetrating the body instead of cutting the tissue. Thus a cavity may be made with no or almost no bleeding. This is an advantage since bleeding may obstruct connection between the implant and the body, increasing the risk of rejection of the implant and/or necrosis of the implant if it is tissue. A blunt penetration tip will also decrease the risk of injuries to the nerves, blood vessels and surrounding tissue.

If desired the implantation tube may have a cross section other than circular, for example a flattened oval cross section. The penetration rod in the kit will have a corresponding cross section fitting inside the implantation tube. In this way it is possible to create a made cavity of desired shape as well as filling the made cavity with a suitable implant so that it fills the made cavity in a desired shape. The made cavity may be filled with a one piece implant suitable for the shape of the made cavity. There is no need for repeated filling of the made cavity. Thus it is possible to control the implantation and the result in an excellent way. The container of the extraction kit can be of soft material to be deformed into the shape of the implantation tube.

The present invention also concerns a kit for extraction of tissue from a body comprising an extraction tube, having a razor or scalpel sharp entrance end, for extraction of tissue and a cutting member or avulsion member for cutting off the tissue to be extracted at the entrance end when the extraction tube is positioned in the body. Also this kit has the advantage of only making one small opening in the skin.

Using such a sharp entrance end of the extraction tube will decrease the risk of any trauma for the tissue to be extracted and thus increase the chance of a successful implantation. In this invention the tissue will be cut out in one segment. A sharp entrance end makes it also possible to extract tissue like muscles, corium, dermis, bone, cartilage in addition to fat. It makes it also possible to extract small dimensions of tissue. Preferably the extraction tube may also be used in the kit for implantation, too, as the container therein.

Preferably the kit comprises a container for housing of the extracted tissue. The container is intended to be positioned inside the extraction tube in use. Preferably this container may also be used in the kit for implantation, too.

In one conceivable embodiment the extraction tube is provided with a separate sharp entrance end. This could be advantageous when the extraction tube is made of a plastic material that might be difficult to sharpen as much as needed in certain applications, for example a syringe. The separate sharp entrance end may be made of a metal suitable for high degree sharpening.

The cutting member may in one embodiment be arranged at the container for cutting off the tissue to be extracted at its entrance end when the extraction tube and container are positioned in the body. It is also conceivable that the cutting member is arranged both in the extraction tube and the container.

In one embodiment the cutting member comprises a suture arranged at the entrance end of the container and at the entrance end of the extraction tube. The method will be to move the container and the extraction tube rotationally relative each other so that a "strangling" of the tissue will be performed and the tissue will be cut off. More examples of different embodiments of the cutting member are described in the detailed description below.

It is also conceivable that the extraction kit comprises a penetration rod if extraction in a specific position is desired, such as extraction of a certain type of tissue. The penetration rod can then be positioned inside the extraction tube (and possible container) for penetrating a way into the specific position without cutting out any tissue. At the specific position the penetration rod is withdrawn and the extraction tube can start to cut out the specific tissue.

The present invention further concerns a tissue transplantation kit for tissue transplantation which comprises an extraction tube, having a razor or scalpel sharp entrance end, for extraction of tissue and a cutting member or avulsion member for cutting off the tissue to be extracted at the entrance end when the extraction tube is positioned in the body. It also comprises a penetration rod that may be positioned inside an implantation tube, for making a cavity in the body. The implantation tube maintains the made cavity. The kit also comprises a container, which is insertable into the implantation tube. The container houses the tissue to be implanted into the made cavity. It is conceivable that the extraction tube constitutes the container.

By means of this kit it will be possible to transplant tissue by only making one small opening in the skin at the extraction site and one small opening at the implantation site of the body. The transplantation kit may also comprise any of the suggested embodiments of the above discussed features for the implantation and extraction kits.

Preferably the inside of the extraction tube, implantation tube and the container have a low friction surface. The lower the friction is the better in order to facilitate the tissue or material to be pushed into the extraction tube or container. The same is true for the leaving of the tissue or material from the implantation tube or container.

The present invention also concerns a method for implanting material into a body. The method is carried out by placing a penetration rod in an implantation tube and then making a cavity in the body with the combination of the penetration rod and implantation tube. Thereafter the penetration rod is removed from the implantation tube and the material to be implanted is inserted into the implantation tube, which tube maintains the made cavity. As a last step the implantation tube is removed.

Preferably the material to be implanted is present in a container which is inserted into the implantation tube when the implantation tube is present in the body maintaining the made cavity. Thereafter both the implantation tube and container will be removed as the last step.

To alleviate the removal of the implantation tube and any container a plunger may be used to keep the material for implantation in place in the last step.

A suture may in one embodiment be connected to the material for implantation in its front end by means of a needle connected to the suture, preferably a suture with a needle in each end. One or both needles are inserted through the implantation tube when it is positioned in the body and out through its front end and further out through the skin so that the material is withheld inside the body in the last step by means of the suture. It is also possible to use both the plunger and the suture. Using a suture makes it also possible to draw the material into place in the made cavity.

The present invention also concerns a method for extracting tissue from a body. The method is carried out by opening the skin of the body and inserting an extraction tube with a razor or scalpel sharp entrance end. Thereafter the tissue to be extracted is cut off at the entrance end of the extraction tube with a cutting member or an avulsion member while the extraction tube is still present in the body. Finally, the extraction tube with the tissue present inside is removed. The extraction tube may also be used in the method for implantation as the container therein.

Preferably a container is inserted into the extraction tube prior to insertion of the extraction tube into the body. The container may also be used in the method for implantation. In the method for extracting tissue one piece of tissue is cut out in a suitable size so it fills a made cavity in a desired shape. There will thus not be any need for repeated filling of the made cavity.

Finally the present invention further concerns a method for transplanting tissue into a body. The method is carried out by opening the skin of the body and inserting an extraction tube. Thereafter the tissue to be extracted is cut off at an entrance end of the extraction tube with a cutting member or an avulsion member while the extraction tube is still present in the body. Then, the extraction tube with the tissue present inside is removed.

As a next step a penetration rod is inserted into an implantation tube and with this combination a cavity is made in the body. Thereafter the penetration rod is removed from the implantation tube and the tissue to be implanted is inserted into the implantation tube, which tube maintains the made cavity. As a last step the implantation tube is removed and the body automatically close around the implanted tissue.

In this way it is possible to create a made cavity of desired shape as well as filling the made cavity with a suitable cut out piece of tissue so that it fills the made cavity in a desired shape. There is no need for repeated filling of the made cavity. Thus it is possible to control the transplantation and the result in an excellent way.

The transplantation method may also comprise any of the suggested steps of the above discussed features for the implantation and extraction methods.

BRIEF DESCRIPTION OF THE DRAWINGS

The present invention will be described in more detail by means of examples of embodiments according to the present invention under referral to the enclosed drawings, in which:

FIG. 9 shows a container in detail, FIG. 10 a and FIG. 10 b show a second embodiment of a cutting member for cutting off tissue to be extracted, FIG. 10 c shows a second embodiment of a cutting member for cutting off tissue to be extracted from above, FIG. 10 d shows a third embodiment of a cutting member for cutting off tissue to be extracted, FIG. 10 e shows a fourth embodiment of a cutting member for cutting off tissue to be extracted, FIG. 10 f shows a fifth embodiment of a cutting member for cutting off tissue to be extracted, FIGS. 10 g(1)-10g(5) show a method of cutting off tissue by means of a cutting member of the fifth embodiment, FIG. 10 h shows a variant of the cutting member of the fifth embodiment, FIG. 10 i shows a variant of the cutting member of the fifth embodiment, FIG. 10 j shows a variant of the cutting member of the fifth embodiment, FIG. 10 k shows a variant of the cutting member of the fifth embodiment, FIG. 10 l and FIG. 10m show a sixth embodiment of a cutting member for cutting off tissue to be extracted, FIG. 10 n and FIG. 10o show a seventh embodiment of a cutting member for cutting off tissue to be extracted.

DETAILED DESCRIPTION OF PREFERRED
EMBODIMENTS OF THE PRESENT
INVENTION

Figure 1:
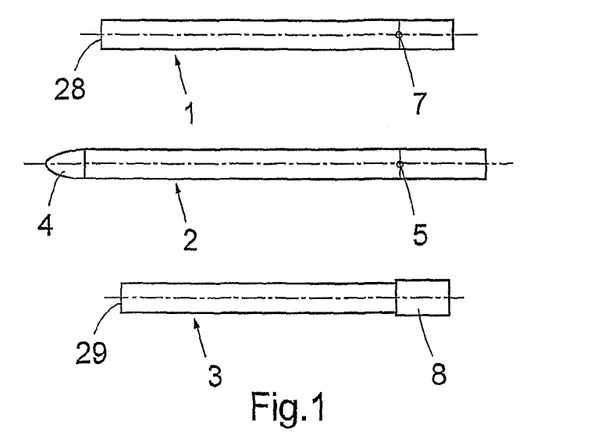
FIG. 1 shows an implantation kit comprising an implantation tube, a penetration rod and a container for housing material to be implanted.

In FIG. 1 an implantation kit comprising an implantation tube 1, a penetration rod 2 and a container 3 for housing material to be implanted is shown. The penetration rod 2 is preferably solid or at least the penetration tip 4 is solid and/or covering the cross section of the rod 2.

Figure 11A:
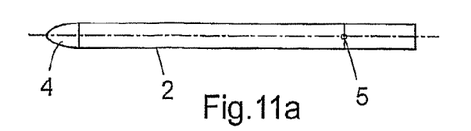
FIG. 11a shows a first embodiment of a penetration rod in detail.
Figure 11B:
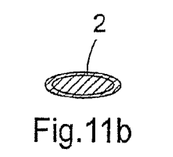
FIG. 11b shows a second embodiment a penetration rod.
Figure 11C:
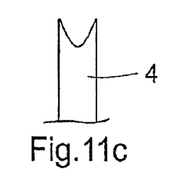
FIG. 11c shows a third embodiment a penetration rod.

See also FIG. 11a, b and c, where FIG. 11a shows a penetration rod 2 in detail and also an enlarged penetration tip 4 showing the preferred embodiment of the penetration tip 4 being blunt. With a blunt penetration tip 4 the penetration rod 2 will separate the tissue while penetrating the body instead of cutting the tissue. Thus a cavity may be made with no or almost no bleeding.

This is an advantage since bleeding may obstruct connection between the implant and the body, increasing the risk of rejection of the implant and/or necrosis of the implant if it is tissue. A blunt penetration tip 4 will also decrease the risk of injuries to the nerves, blood vessels and surrounding tissue. The penetration rod 2 may be provided with some kind of connection means 5, such as a recess 5 as shown, for connection with the implantation tube 1.

The cross section of the penetration rod 2 may be circular, or have any other suitable shape such as a flattened oval as shown in FIG. 11b, all dependent on how the cavity to receive the implant shall be. The penetration rod 2 may be straight but it is also possible that it is slightly bent along its longitudinal direction (not shown).

In case of implanting at a position in the body where it is difficult to disconnect tissue from each other, for example inside dermis/corium or between dermis/corium and bone, another type of penetration tip 4 might be needed, for example a sharp tip and/or a fork type tip 4' as shown in FIG. 11c.

Figure 14:
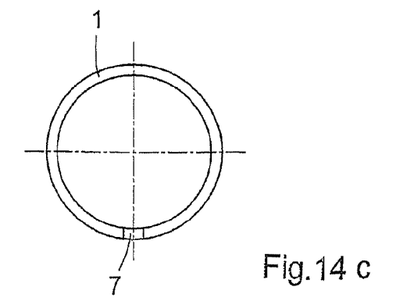
Figure 14A:
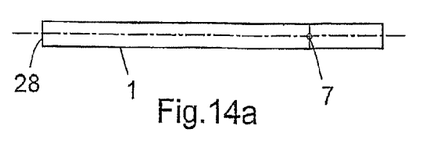
FIG. 14a shows a first embodiment of an implantation tube in detail, FIG. 14 b and FIG. 14c show a second embodiment of an implantation tube.
Figure 14B:
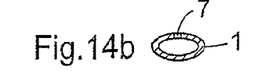

The implantation tube 1 is shown in more detail in FIGS. 14 a and b. It is preferably a tube having a circular cross section although it is also conceivable that the implantation tube 1 has the same cross section as the penetration rod 2 or is ductile so that it can adjust to the shape of the penetration rod 2. A front end 28 is the end which is inserted into a body. Preferably the implantation tube is smooth inside in order to give a low friction coefficient.

In FIG. 14b an implantation tube 1 having a flattened oval cross section shown, which is suitable for the penetration rod shown in FIG. 11b. Preferably the implantation tube 1 is provided with some kind of connecting means for connecting with the penetration rod 2. In the shown embodiment a hole 7 is present in the implantation tube 1, preferably near the outer end 8 of the implantation tube 1. When a flattened oval penetration rod 2 and a corresponding implantation tube is used the made cavity will be given a corresponding shape and the implant will fill this space. In this way it is possible to control the implantation and to change the cavities for each specific case.

Another conceivable embodiment of the implantation tube 1 has some kind of see-through portion (not shown) so that the amount of implant is visible through the portion. It is also possible to have a measurement scale for length or volume along the length of the extraction tube 9 and/or any see-through portion, see FIG. 16a.

Figure 3:
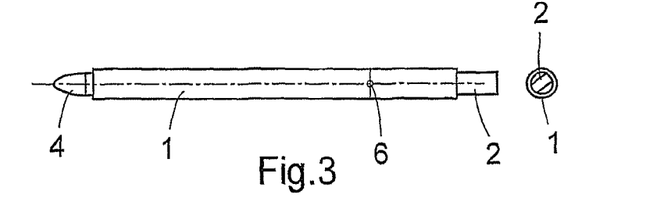
FIG. 3 shows the combination of a penetration rod inserted in an implantation tube and the cross section thereof.

In FIG. 3 it is shown when the penetration rod 2 is situated inside the implantation tube 1. The two pieces 2, 1 are interconnected for example by means of a pin 6 inserted through the hole 7 in the implantation tube 1 and into or through the penetration rod 5.

Figure 9:
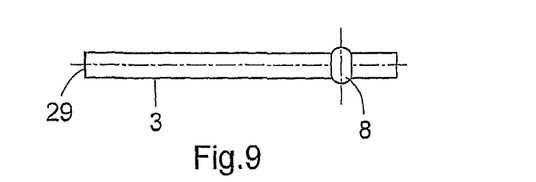
Figures 10A, 10B:
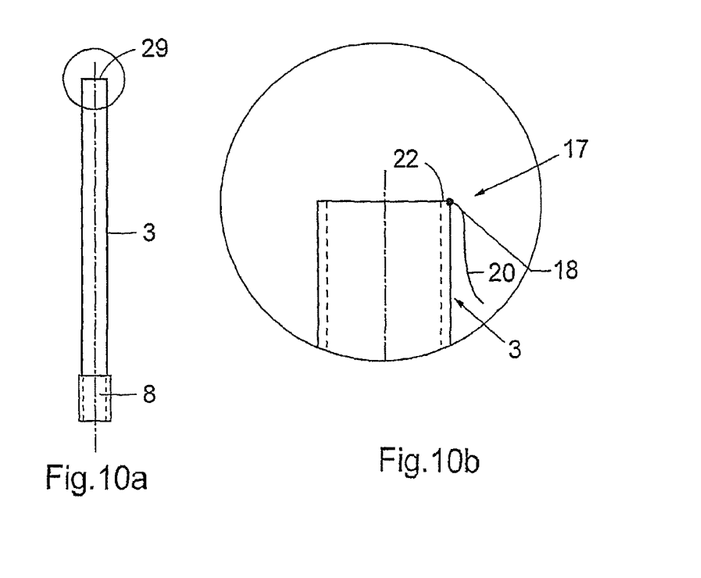
Figure 10C:
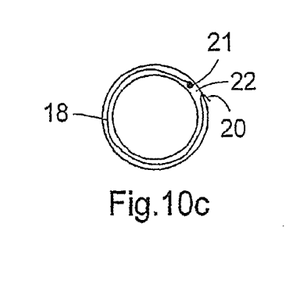
Figure 10D:
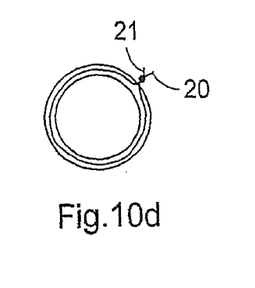
Figure 10E:
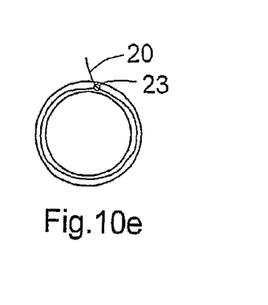

The container 3 in FIG. 1 is also shown in more detail and different embodiments in FIGS. 9 and 10a. The container 3 is preferably a thin-walled tube and is preferably provided with a stop 8, for example in the shape of a bulb as in FIG. 9 or as an extra outer tubing as in FIG. 10a, in order not to let the container be inserted to deep into the implantation tube 1 or an extraction tube 9, which will be described below. An entrance end 29 is situated at the opposite end to the stop 8.

The cross section of the container 3 may be circular or any other suitable shape or it could be made of a ductile material so that the container 3 can be inserted into for example an implantation tube 1 having another cross section and thus take up the shape of the implantation tube 1. For example the container 3 can be made of a plastic suitable for medical use.

It is also conceivable with an embodiment of a container 3 having some kind of see-through portion (not shown) so that the amount of implant is visible through the portion. It is also possible to have a measurement scale for length or volume along the length of the container 3 and/or any see-through portion (not shown).

Figure 2:
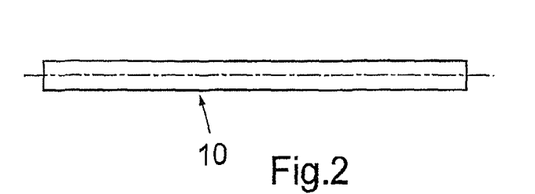
FIG. 2 shows a plunger suitable for incorporation into the implantation kit shown in FIG. 1.
Figure 12A:
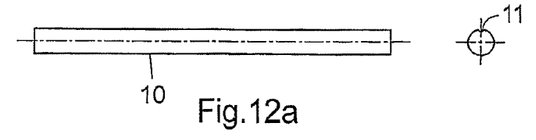
FIG. 12a shows a plunger in detail.

In the implantation kit it is preferred to have a plunger 10, too. It is preferably a solid rod, see FIG. 2 and the more detailed FIG. 12a, having a channel 11 along its length at the periphery. When the plunger 10 cooperates with the extraction tube 1 and/or the container 3, air may flow in the channel 11.

Figure 12B:
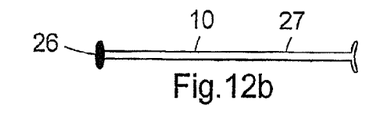
FIG. 12b shows a second embodiment of a plunger.

The plunger 10 may instead have a plunger portion 26 being slightly smaller in cross section than the inside of the implantation tube 1 and/or the container 1. The rest of the length of the plunger may have a smaller cross section than the plunger portion 26, like a stick 27, see FIG. 12b.

Figure 4:
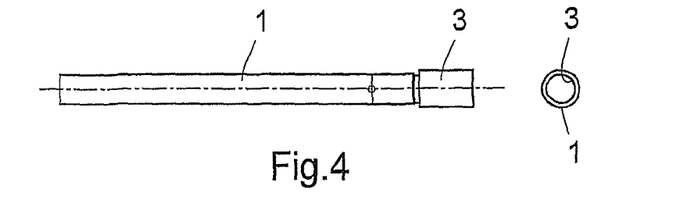
FIG. 4 shows the combination of a container inserted in an implantation tube and the cross section thereof.
Figure 13:
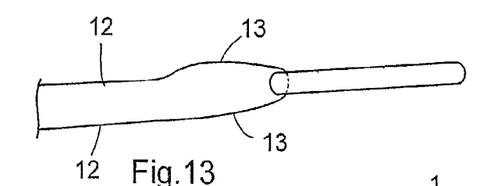
FIG. 13 shows a suture, having two needles, connected to a piece of material to be implanted.

It is also conceivable to incorporate a needle 12 and suture 13, see FIG. 13, to the implantation kit for connection to the material to be implanted. In FIG. 4 it is shown when the container 3 is situated inside the implantation tube 1.

When using the implantation kit according to the present invention the penetration rod 2 is inserted into the implantation tube 1 and they are preferably connected to each other. An opening in the skin is made if necessary and the combination of implantation tube 1 and penetration rod 2 is inserted into the body at a desired place making a cavity in the body. When the combination of implantation tube 1 and penetration rod 2 is at the desired position in the body the penetration rod 2 is withdrawn.

The implantation tube 1 stays in the body and maintains the cavity made by the combination. Thereafter the material to be implanted is inserted into the implantation tube 1 and the implantation tube 1 is withdrawn from the body leaving the material to be implanted inside the body. Preferably the material to be implanted is present in the container 3. Thus, the container 3 is inserted into the implantation tube 1 and both the implantation tube 1 and the container 3 are withdrawn from the body leaving the material to be implanted inside the body.

In order to alleviate the withdrawal of the implantation tube 1 and the possible container 3 and still keeping the material to be implanted in the made cavity in the body the plunger 10 may be used to keep the material in place. For example this can be done by inserting the plunger 10 in the outer end of the implantation tube 1 and the outer end of the container 3 when used while withdrawing the implantation tube 1 and the container 3 if used along the outside of the plunger 10.

Another way to alleviate the withdrawal of the implantation tube 1 and the container 3 if used is to use a suture 13 that is connected to the material to be implanted in its front end, see FIG. 13.

The suture 13 is preferably provided with a needle 12 at each end. The suture 13 may be drawn through the front end of the material to be implanted and the two needles 12 are inserted through the implantation tube 1 when it is positioned in the body and out through its inner end and further out through the skin. Thus the material to be implanted may be drawn into place or withheld inside the body during the withdrawal by means of the suture 13. When the implant is in position one of the suture 13 is cut so that one needle comes off and the suture 13 may be withdrawn from the body in two parts. The suture 13 may be combined with the use of the plunger 10 if desired.

An important advantage with this implantation kit and method is that it will only make one wound in the body. If the needles 12 and suture 13 are used it is obvious that the needle stick will not cause such a wound.

Figure 5:
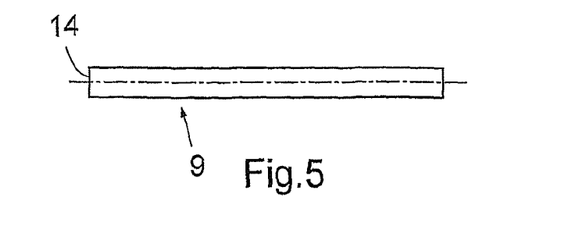
FIG. 5 shows an extraction tube having a razor or scalpel sharp entrance end.
Figure 8A:
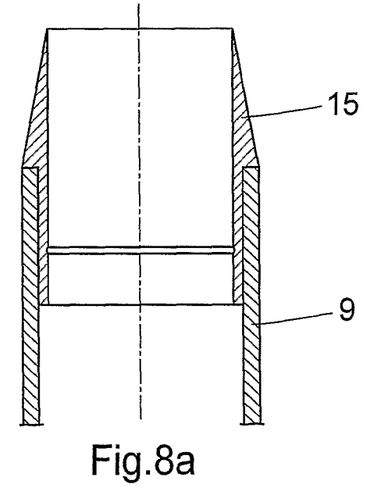
FIG. 8a shows a second embodiment of the sharp entrance end of an extraction tube.
Figure 8B:
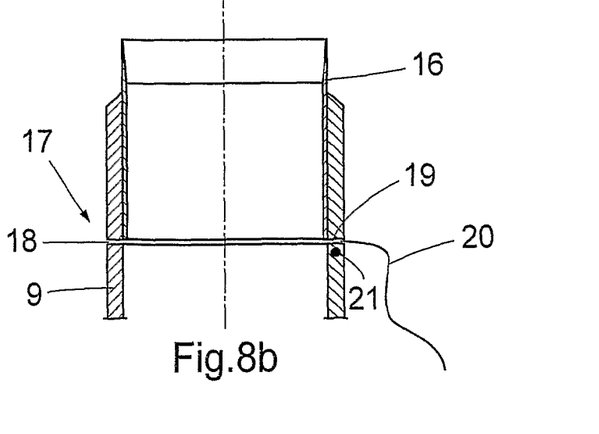
FIG. 8b shows a third embodiment of the sharp entrance end of an extraction tube and a first embodiment of a cutting member for cutting off tissue to be extracted.

In FIG. 5 an extraction tube 9 having a razor or scalpel sharp entrance end 14 is shown. It is also conceivable to have an obliquely cut entrance end 14 (not shown). In FIGS. 8a and b other embodiments of an extraction tube 9 are shown. The cross section of the extraction tube 9 is preferably circular since it is easier to extract tissue while manually rotating the extraction tube 9. Preferably the extraction tube 9 is smooth inside in order to give a low friction coefficient. The extraction tube 9 is for example usable in the implantation kit, too, constituting the container 3.

For extracting tissue the skin of a body is opened and the extraction tube 9 is inserted into the opening, preferably in a manually rotational way, or with the aid of a drill equipment. When a suitable amount of tissue has filled the extraction tube 9 a cutting member 17 will cut off the tissue to be extracted close to the entrance end 14. The cutting member 17 will be described below.

The entrance end 14 has a sharp edge, which could be made by sharpening the extraction tube 9 itself at the entrance end 14, as in FIG. 5, or by providing a separate cutter 15, for example like the cutter 15 shown in FIG. 8a. In a further embodiment, see FIG. 8b or 16a, a trephine blade 16 is arranged at the entrance end 14 of the extraction tube 9 in order to make a sharp entrance end 14. As mentioned before the cutter 15 or trephine 16 may be oblique (not shown).

In order to have a suitable filling capacity the entrance end may be straight, as shown, or have a larger diameter, like a funnel, in order to capture maximum volume of a soft tissue. It is also conceivable to have a smaller end diameter in order to decrease the risk of hard or harder tissue to get stuck.

Another conceivable embodiment of the extraction tube 9 has some kind of see-through portion so that the amount of implant is visible through the portion. It is also possible to have a measurement scale for length or volume along the length of the extraction tube 9 and/or any see-through portion, see FIG. 16a.

In FIG. 8b a separate feature is also shown. This feature concerns a cutting member 17 for cutting off tissue to be extracted. This cutting member 17 may of course be arranged at any suitable embodiment of the extraction tube 9.

The cutting member shown in FIG. 8b comprises a suture 18 or the like provided along the inner diameter of the extraction tube 9. It could be releasably held in place for example by being squeezed between the trephine blade 16 or cutter 15 and the extraction tube 9. Or it could be releasably held in place for example by means of any suitable adhesive.

One end 20 of the suture 18 is running through a hole 19 in the extraction tube 9 and along the outside of the extraction tube 9 at least about the same length as the extraction tube 9. It is also conceivable to let the long end 20 of the suture 18 run along the inside of the extraction tube 9. The opposite end 21 of the suture 18 is preferably fixed in the wall of the extraction tube 9.

When the extraction tube 9 is positioned inside a body and a suitable amount of tissue is present inside the extraction tube 9 the surgeon grips the long end 20 of the suture 18 and draws it outwards. The loop of the suture 18 inside the extraction tube 9 will loosen and "strangles" the tissue so that the tissue will be cut off.

Figure 6:
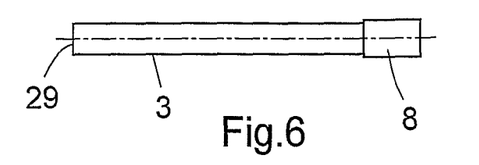
FIG. 6 shows a container suitable for incorporation into a extraction kit comprising the extraction tube shown in FIG. 5.

Preferably an extraction kit also comprises a container 3, see FIG. 6, which for example is usable in the implantation kit, too. The container 3 in FIG. 6 is also shown in more detail and different embodiments in FIGS. 9 and 10a. The container 3 is preferably a thin-walled tube and is preferably provided with a stop 8, for example in the shape of a bulb as in FIG. 9 or as an extra outer tubing as in FIG. 10a, in order not to let the container be inserted too deeply into the implantation tube 1 or the extraction tube 9. The container 3 has preferably an outer diameter just smaller than the inner diameter of the extraction tube 9.

Figure 7:
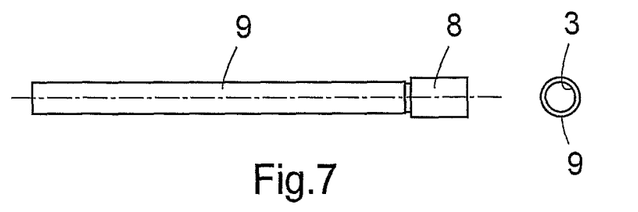
FIG. 7 shows the combination of a container inserted into a extraction tube and the cross section thereof.

When the container 3 is used in the extraction kit it will be positioned inside the extraction tube 9, see FIG. 7, before extraction of the tissue will start. For extracting tissue the skin of a body is opened and the extraction tube 9 with the container is inserted, preferably in a manually rotational way. Preferably the container 3 is smooth inside in order to give a low friction coefficient.

When a suitable amount of tissue has filled the extraction tube 9 and container 3 a cutting member 17 will cut off the tissue to be extracted close to the entrance end 14. One embodiment of a cutting member 17 arranged at the extraction tube 9 is described above, further cutting members will now be described.

In FIG. 10a a suture 18 or the like provided along an edge 22 around the diameter of the container 3 forming a second embodiment of a cutting member 17 for cutting off tissue to be extracted. It could be releasably held in place for example by means of any suitable adhesive.

See also FIG. 10b, which shows the cutting member 17 and a top view of the container 3. One longer end 20 of the suture 18 is running along the outside of the container 3 at least about the same length as the container 3. The opposite end 21 of the suture 18 is preferably fixed in the wall of the container 3.

When the extraction tube 9 and the container 3 is positioned inside a body and a suitable amount of tissue is present inside the extraction tube 9 and the container 3 the surgeon grips the long end 20 of the suture 18 and draws it outwards. The loop of the suture 18 inside the extraction tube 9 will loosen and "strangles" the tissue so that the tissue will be cut off.

It is also possible to let both of the ends 20, 21 of the suture 18 run along the length of the container 3 at its outside, see the third embodiment shown in FIG. 10 *d*. Or, instead of fixing the end 21 in the container 3, the end 21 could be in the shape of a small loop 23 as shown a fourth embodiment in FIG. 10 *e*. Said cutting member embodiments are suitable for the extraction tube 9, too.

Another conceivable embodiment of the cutting member 17 is shown in FIG. 10 *f*. In this fifth embodiment the suture 18 is fixed with one end 24 in the extraction tube 9 and the other end 25 is fixed in the container 3, both preferably close to the entrance end 14. For example the suture 18 can be releasably held at the edge 22 of the container 3 by means of a suitable adhesive.

Figure 10F:
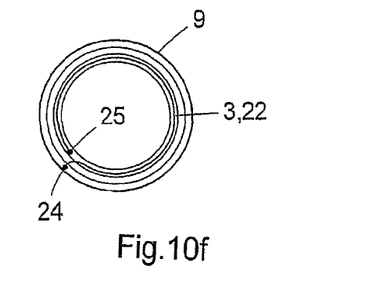
Figure 10G:
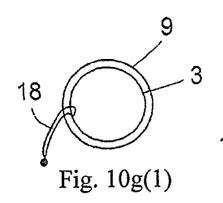

When the extraction tube 9 and the container 3 is positioned inside a body and a suitable amount of tissue is present inside the extraction tube 9 and the container 3 the surgeon starts a relative rotational movement between the extraction tube 9 and the container 3, for example rotates the container 3 inside the extraction tube 9. The suture 18 will loosen and twists around the tissue so that the tissue will be cut off.

A tissue cutting method is shown in FIGS. 10(*g*)(1) to 10(*g*)5, although showing a variant of cutting member, which is shown in FIG. 10 *k*. When a relative rotational movement starts between the container 3 and the extraction tube 9, the suture 18 will start to cross over the cross section of the container 3. In FIGS. 10(*g*)(1) to 10(*g*)5 it is shown, for clarity reasons, how the extraction tube 9 is rotated, although in practice it might be more common to rotate the container 3. After 1½ revolutions a strangling loop 44, see FIGS. 10(*g*)(1) to 10(*g*)5, has been built up, which will "strangle" the tissue more and more the more relative rotational movement is carried out.

Figure 10H:
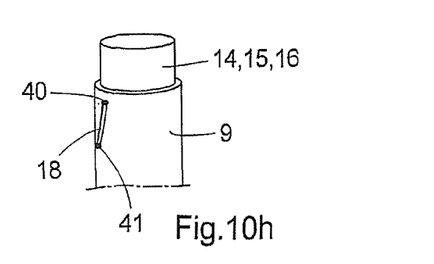

There are conceivable different variants of the fifth embodiment of the cutting member. As shown in FIG. 10 *h* an extraction tube 9 has a through going hole 40 through which a suture 18 may run. The suture 18 is for example provided with a stop or knot 41 at the portion positioned outside the extraction tube 9. The stop or knot 41 is larger than the through going hole 40 in order to make the suture 18 stay attached to the extraction tube 9 during a cutting off of the tissue.

Figure 10I:
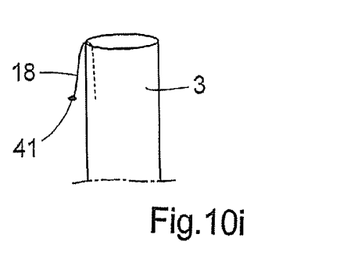
Figure 10J:
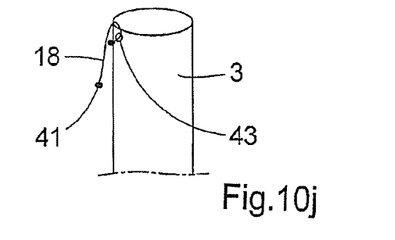
Figure 10K:
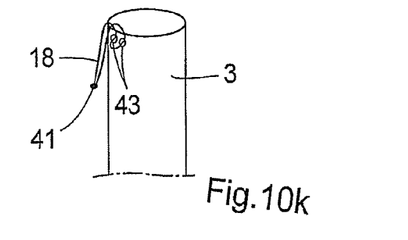

The suture 18 is also attached to the container 3. For example, the suture 18 may be glued to the inside of the container 3, see FIG. 10 *i*, or by means of a second stop or knot 42, see FIG. 10 *i*. The second stop or knot 42 is preferably positioned on the outside of the container 3 in order not to distract the extraction of tissue. If so positioned, the suture 18 run through a through going hole 43 positioned close to the entrance end and up out over the rim of the container 3. The portion outside the container 3 is then going through the through going hole 40 of the extraction tube 9. For clarity reasons the extraction tube 9 is not shown in FIGS. 10 *i-k*.

Another conceivable connection of the suture 18 to the extraction tube 9 and container 3 is to provide the container 3 with two through going holes 43, see FIG. 10 *k*, and letting the suture 18 make up a loop which has a stop or a knot 41 at the outside of the extraction tube 9. It is also conceivable that also the extraction tube has two through holes 40, whereby the loop of the suture 18 only needs to be tied together in the ends, preferably outside the extraction tube.

Tests have shown that cutting members according to the fifth embodiment and the corresponding method of cutting off tissue by "strangling" are advantageous. They are easy to produce and easy to handle. There is no need of drawing any sutures or strings along the length of the extraction tube or container. Neither over any end surface deflecting the suture or string about 90 degrees, which could cause the suture or string to get caught or be torn off or at least cause a high friction counter force.

In FIGS. 10 *l* and *m* a further embodiment of a cutting member is shown. A thin-walled cutting tube 35, preferably of metal, is positioned on the outside of the extraction tube 9. The end closest to the entrance end 14 of the extraction tube 9 is cut axially or obliquely to the length axis into flaps 36. The flaps 36 are prebent or biased radially towards the central length axis. The cutting tube 35 is preferably shorter than the extraction tube 9.

Figure 10L:
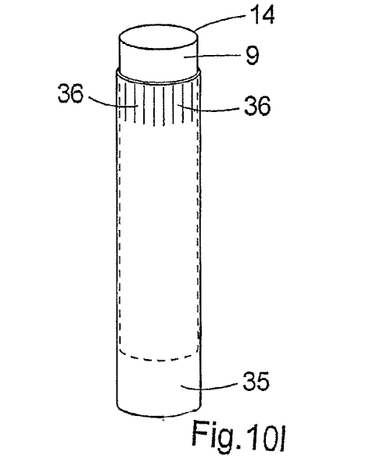
Figure 10M:
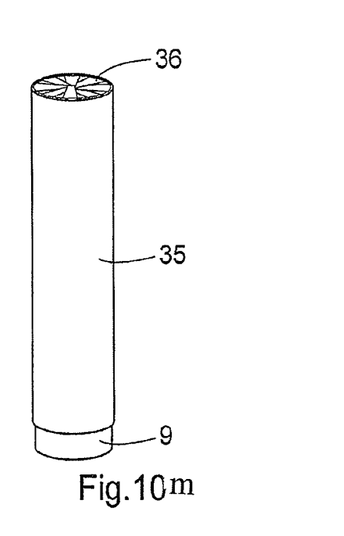

When then a sufficient amount of tissue is present inside the extraction tube 9 the cutting tube 35 is pushed towards the entrance end 14 and when the flaps 36 are no longer stopped by the extraction tube 9 they will bend radially inwards over the entrance end 14, thereby cutting off the tissue to be extracted.

In FIGS. 10 *n* and *o* a further embodiment of a cutting member is shown. A hose 37 provided with a contractable ring 38 is provided on the outside of the extraction tube 9. The contractable ring 38 is provided close to the entrance end 14 of the extraction tube 9. A pushing tube 39 is positioned between the hose 37 and the extraction tube 9 a bit further away from the entrance end 14 than the contractable ring 38.

Figure 10N:
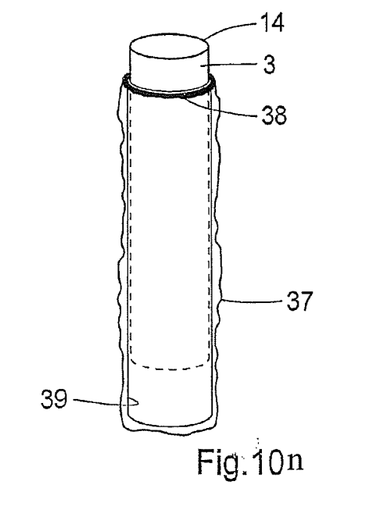
Figure 10O:
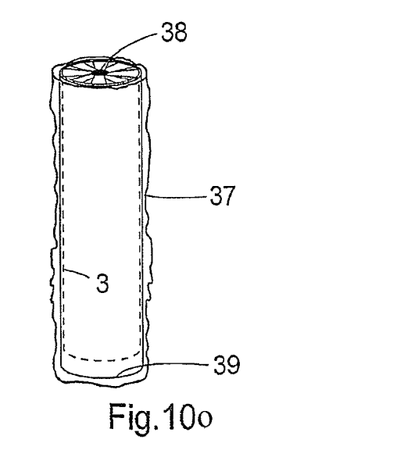

When then a sufficient amount of tissue is present inside the extraction tube 9 the pushing tube 39 is pushed towards the entrance end 14 pushing the contractable ring 38 over the edge at the entrance end 14 whereby the ring contracts and cuts off the tissue to be extracted.

Figure 16A:
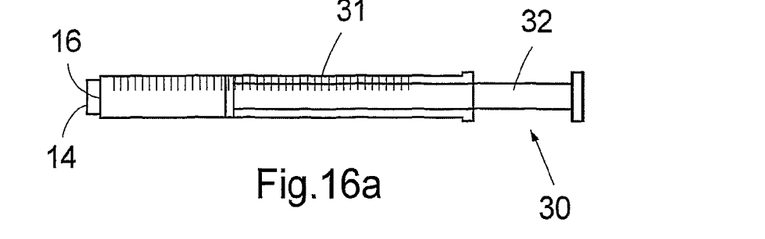
FIG. 16a shows an extraction tube made of a syringe with a razor or scalpel sharp entrance end.
Figure 16B:
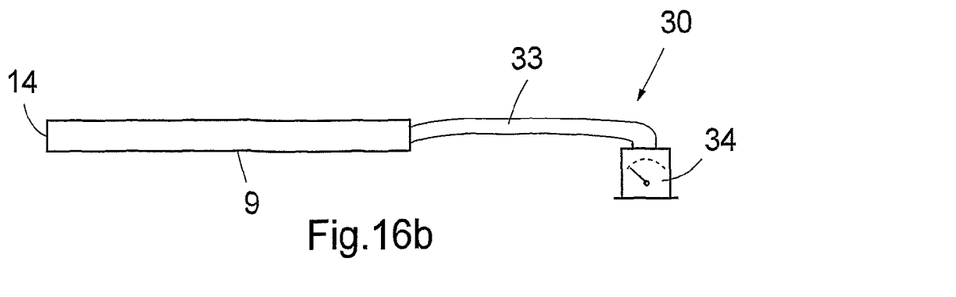
FIG. 16b shows an extraction tube connected to an avulsion member exerting a negative pressure to the end of the extraction tube situated opposite the entrance end.

In another embodiment, see FIGS. 16*a* and *b*, the extraction tube 9 comprises an avulsion member 30. In FIG. 16*a* a syringe 31 constitutes the extraction tube 9 and is provided with a sharp entrance end, in the shown case a trephine 16. When a desired amount of tissue is extracted and present inside the extraction tube 9 a syringe piston 32 will be slightly further withdrawn exerting a negative pressure to the tissue keeping it inside the extraction tube 9 while tearing off the tissue at its inner end.

The syringe piston 32 could be used as the plunger 10 if the syringe 31 constitutes the container 3 of the implantation kit. In another embodiment it is conceivable to be able to remove the sharp entrance end, for example the trephine 16.

In FIG. 16*b* the extraction tube 9 is connected to an avulsion member 30 comprising a tubing 33 and a negative pressure providing apparatus 34. Preferably the negative pressure providing apparatus 34 is adjustable and automated and thus may provide desired amounts of negative pressure for each occasion.

By providing negative pressure in the extraction tube 9 during extraction the filling of the extraction tube 9 will be alleviated, which may be desired especially when extracting harder tissue or when small dimensions of tissue are extracted.

It is also conceivable that the extraction kit comprises a penetration rod 2 if extraction in a specific position is desired, such as extraction of a certain type of tissue. The penetration rod 2 can then be positioned inside the extraction tube 9 (and possible container 3) for penetrating a way into the specific position without cutting out any tissue. At the specific position the penetration rod 2 is withdrawn and the extraction tube 9 can start to cut out the specific tissue.

Figure 15A:
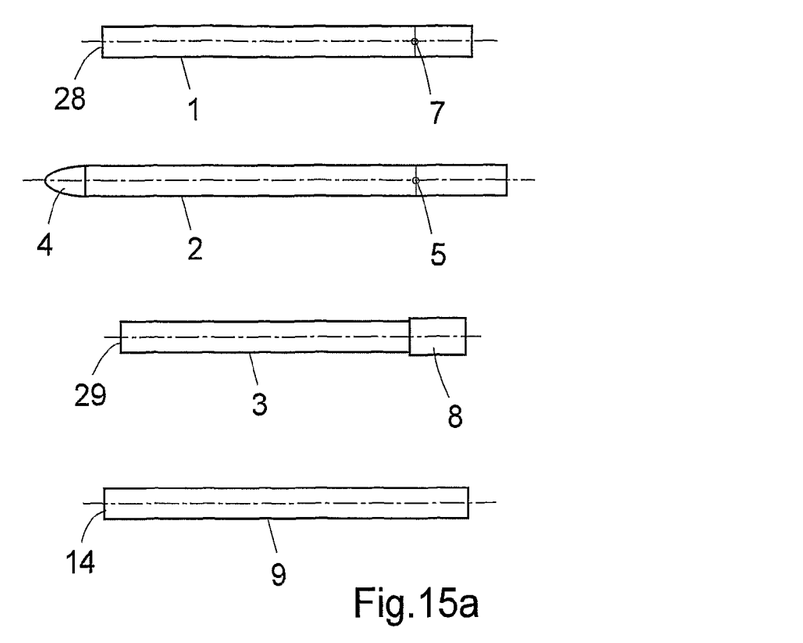
FIG. 15a shows a transplantation kit comprising an implantation kit according to FIG. 1 and an extraction kit according to FIG. 5.
Figure 15B:
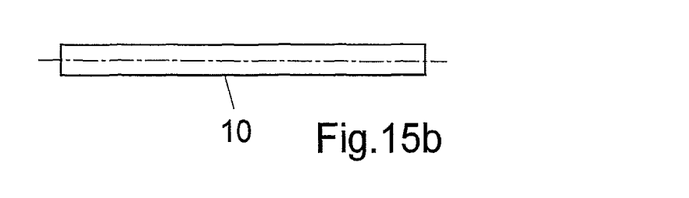
FIG. 15b shows a plunger suitable for incorporation into the transplantation kit.

In FIG. 15a a transplantation kit is shown comprising an extraction tube 9, a container 3, an implantation tube 1 and a penetration rod 2. In FIG. 15b also a plunger 10 is incorporated in the transplantation kit.

When transplanting tissue from preferably one site of the body into a second site of the body, an extraction tube 1 is inserted into the first site of the body, preferably in a manually rotational way. When a suitable amount of tissue has filled the extraction tube 9 a cutting member 17 or avulsion member 30 will cut off the tissue to be extracted close to the entrance end 14. Thereafter the extraction tube 9 is removed from the body bringing out the extracted tissue.

At the desired site of the body for the implantation the skin is preferably opened and the penetration rod 2 present inside the implantation tube 1 is inserted into the body making a cavity for the tissue to be implanted. Thereafter the penetration rod 2 is removed leaving the implantation tube 1 in the body to maintain the made cavity. The extracted tissue to be implanted from the extraction tube 9 is inserted into the implantation tube 1 and finally the implantation tube 1 is removed from the body leaving the implanted tissue in the made cavity.

Preferably the container 3 is used in the method. If so, it will be positioned inside the extraction tube 9 prior to insertion of the extraction tube 9 into the body so that the extracted tissue will become present in the container 3.

When having the extracted tissue in the container 3 it is preferred to implant the extracted tissue by using the container 3. Thus the container 3 with the extracted tissue is removed from the extraction tube 9 and inserted into the implantation tube 1 when the implantation tube 1 is present in the made cavity. Thereafter both the implantation tube 1 and the container 3 will be removed from the body leaving the implanted tissue in the made cavity.

In another preferred method for transplanting tissue the plunger is also used to keep the tissue in place while removing the implantation tube 1 and any container 3. Instead, or also, a suture 13 is connected to the tissue and one or two needles 12 are inserted through the implantation tube 1 when it is positioned in the body and out through its entrance end 14 and further out through the skin so that the tissue may be drawn into place or withheld inside the body by means of the suture while removing the implantation tube 1 and any container 3.

The invention claimed is:

1. A tissue transplantation method for extracting tissue from a first site of a body and implanting the extracted tissue into a second site of the body, comprising the steps of:
   opening the skin of the body at the first site of the body, inserting an extraction tube into the opening of the skin;
   thereafter, cutting off the tissue to be extracted at an entrance end of the extraction tube with a cutting member or avulsion member while the extraction tube is present in the body;
   subsequently, removing the extraction tube with the tissue present inside;
   thereafter, placing a penetration rod having a blunt penetration tip in an implantation tube;
   subsequently, making a cavity in the body at a second site with the combination of the penetration rod and a first end of the implantation tube;
   thereafter, removing the penetration rod from the implantation tube;
   thereafter, inserting the extracted tissue to be implanted into a second end of the implantation tube, which tube is disposed in and maintains the made cavity; and
   as a last step, removing the implantation tube from the cavity, leaving the tissue to be implanted in the cavity of the body.

2. The method according to claim 1, further comprising inserting the extraction tube comprising the extracted tissue to be implanted into the second end of the implantation tube.

3. The method according to claim 1, further comprising inserting a container into the extraction tube prior to the insertion of the extraction tube into the body at the first site.

4. The method according to claim 3, further comprising inserting the container comprising the extracted tissue to be implanted into the second end of the implantation tube.

5. The method according to claim 1, further comprising using a plunger to keep the extracted tissue for implantation in place in the last step of removing the implantation tube.

6. The method according to claim 3, further comprising cutting off the tissue to be extracted at the entrance end of the extraction tube using a suture arranged between the entrance end of the container and the extraction tube.

7. The method according to claim 1, further comprising providing a negative pressure in the extraction tube when extracting tissue.

8. The method according to claim 1, further comprising connecting a suture to the front end of the extracted tissue for implantation in its front end and connecting at least one needle to the suture, then inserting the needle through the implantation tube when the implantation tube is positioned in the body and out through the implantation tube's front end and further out through the skin so that the extracted tissue may be drawn into place or withheld inside the body in the last step by means of the suture.

9. A method for transplanting tissue of a body, using a tissue transplantation kit, wherein the tissue transplantation kit comprises:
   an extraction kit comprising an extraction tube having a sharp entrance end, for extraction of tissue and a cutting member or avulsion member for cutting off the tissue to be extracted at the entrance end when the extraction tube is positioned in the body, the extraction tube comprising a container for housing the extracted tissue, and
   an implantation kit comprising an implantation tube, a penetration rod and the container, the penetration rod being blunt in its penetration tip and positionable inside the implantation tube for making a cavity in the body, the implantation tube maintains the made cavity, the container being insertable into the implantation tube when the penetration rod is not present therein,
   the method comprising the steps of:
   opening the skin of the body at a first site of the body, inserting the extraction tube into the opening of the skin;
   thereafter, cutting off the tissue to be extracted at the entrance end of the extraction tube with the cutting member or avulsion member while the extraction tube is present in the body;
   subsequently, removing the extraction tube with the tissue present inside;
   thereafter, placing the penetration rod having the blunt penetration tip in the implantation tube;
   subsequently, making a cavity in the body at a second site of the body with the combination of the penetration rod and a first end of the implantation tube;
   thereafter, removing the penetration rod from the implantation tube;
   thereafter, inserting the extracted tissue to be implanted into a second end of the implantation tube, which tube is disposed in and maintains the made cavity; and as a last step, removing the implantation tube from the cavity, leaving the tissue to be implanted in the cavity of the body.

* * * * *